Figure 1:
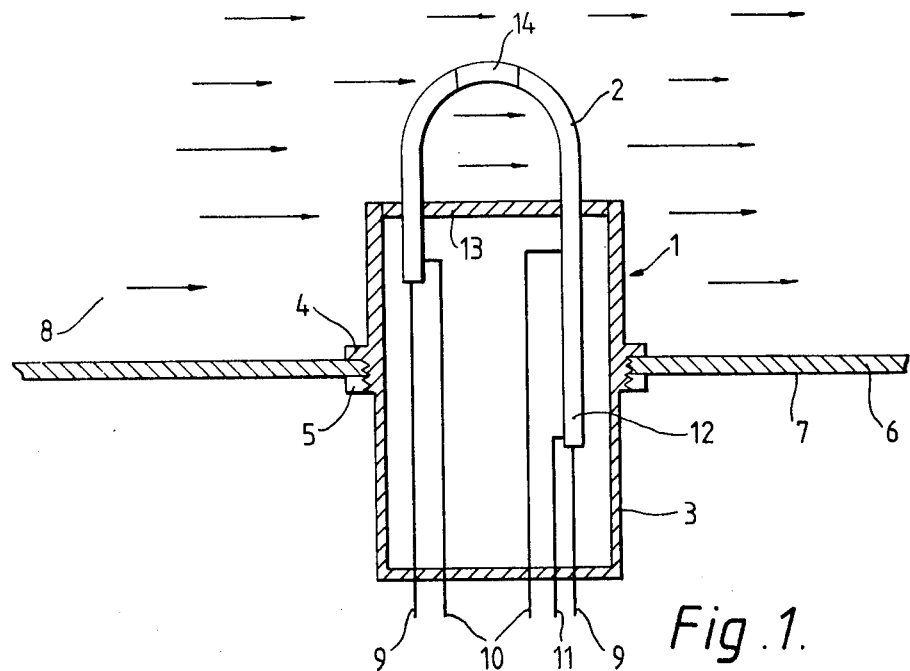

United States Patent [19]

Conlon et al.

[11] 4,412,174
[45] Oct. 25, 1983

[54] MONITORING OF CORROSION

[75] Inventors: Thomas W. Conlon, Abingdon; Constantin Edeleanu, Cambridge, both of England

[73] Assignee: United Kingdom Atomic Energy Authority, London, England

[21] Appl. No.: 267,656

[22] Filed: May 27, 1981

[30] Foreign Application Priority Data

May 30, 1980 [GB] United Kingdom ............... 8017670

[51] Int. Cl.$^3$ ........................................... G01R 27/02
[52] U.S. Cl. ............................... 324/65 CR; 250/303; 250/359.1
[58] Field of Search ....................... 324/65 CR, 65 P; 250/303, 359.1

[56] References Cited

U.S. PATENT DOCUMENTS

| | | | |
|---|---|---|---|
| 2,994,778 | 8/1961 | Marsh | 250/303 |
| 3,101,413 | 8/1963 | Schaschl et al. | 250/303 X |
| 3,599,090 | 8/1971 | Fitzpatrick et al. | 324/65 CR X |
| 3,898,459 | 8/1975 | Lechman et al. | 250/303 |
| 4,027,157 | 5/1977 | Gerve et al. | 250/303 |

FOREIGN PATENT DOCUMENTS

| | | | |
|---|---|---|---|
| 2425113 | 10/1975 | Fed. Rep. of Germany | 250/303 |
| 437950 | 1/1975 | U.S.S.R. | 250/303 |
| 724991 | 3/1980 | U.S.S.R. | 324/65 CR |

*Primary Examiner*—Stanley T. Krawczewicz
*Attorney, Agent, or Firm*—Larson and Taylor

[57] ABSTRACT

A method of and apparatus for the detection of pitting corrosion, in which simultaneous measurements of the rate of loss of material from a body under test are made by means of changes in the resistance of the body and thin layer activation analysis. If the body is corroding uniformly, the rate of loss of material as measured by each technique is the same; if pitting corrosion is occuring, then the two measured rates of loss of material are different.

8 Claims, 2 Drawing Figures

MONITORING OF CORROSION

The present invention relates to the monitoring of corrosion, and in particular to the detection of pitting corrosion.

A metal surface which is exposed to a corrosive environment can suffer two forms of corrosion. The first form of corrosion occurs uniformly over the surface, but the second form of corrosion is localised. This form of attack is known as pitting corrosion. It is more serious than uniform corrosion because whereas it can take a long time for uniform corrosion to reduce the thickness of a body of the material of which the surface forms part to a point where its mechanical strength is destroyed, pitting corrosion can lead rapidly to puncturing of the body of material with whatever consequences may flow from such an occurrence.

Measurement techniques which have been developed for detecting and measuring uniform corrosion have been found to be unsatisfactory when attempts have been made to apply them to the detection and measurement of pitting corrosion. For example, a known technique for measuring corrosion is to compare the resistance of an element which is exposed to a corrosive environment with that of an identical element in the same situation but protected from the corrosive environment. Changes in the ratio of the resistances of the two elements give a measurement of changes in the cross-section of the exposed element due to corrosion. This technique is incapable of telling (without visual inspection) whether the changes in cross-section are localised or widespread, and hence cannot distinquish between pitting and uniform corrosion.

Thus, a phenomenon which is a major cause of plant failure is for practical purposes beyond the scope of instrumental detection and measurement.

According to the present invention, there are provided a method of and apparatus for the detection and measurement of pitting corrosion in a corrosive environment, the method comprising the operations of exposing to the corrosive environment a corrodible element a surface region of which has been rendered radioactive, measuring changes in a parameter of the element which is susceptible to the effects of corrosion of the element, simultaneously either measuring changes in the activity of the element or the growth of activity at a station down stream of the element, deriving from both sets of measurements indications of the rate of removal of corroded material from the element and comparing the indicated rates of removal of material from the element, and the apparatus comprising, means for supporting in a flowing corrosive environment a corrodible element a surface region of which is arranged to be radioactive, means for measuring changes in a parameter of the element as a result of corrosion of the element and deriving therefrom a first signal representative of the rate of corrosion of the element, means for measuring either changes in the activity of the element or the growth of activity at a station down stream of the element and deriving a second signal therefrom indicative of the rate of removal of active material from the element, and means for comparing the first and second signals.

Preferably the parameter of the element which is susceptible to the effects of corrosion which is monitored is the resistance of the element.

A suitable way of producing the surface region of the element which is radioactive is to subject it to bombardment by radiation having an energy sufficient to cause nuclear reactions within the surface of the said region of the element.

Figure 2:
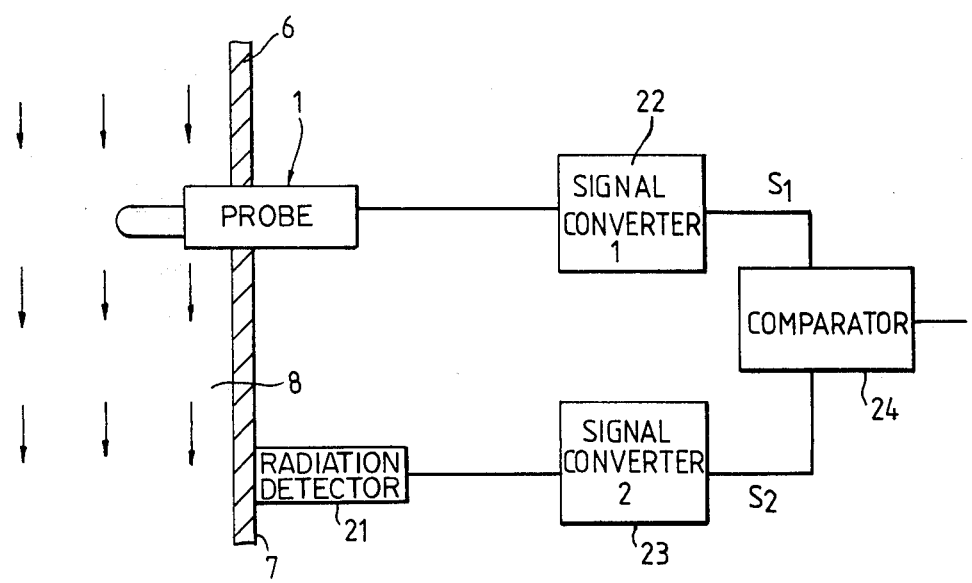

The invention will now be described, by way of example, with reference to the accompanying drawing in which FIG. 1 is a diagrammatic representation of a probe device for use in carrying out the present invention, and FIG. 2 is a diagrammatic representation of an apparatus embodying the invention.

Referring to FIG. 1, a corrosion monitoring probe 1 consists of a U-shaped element 2 made of a conducting corrodible material which is mounted in a noncorrodible sealed base 3.

The base 3 has a collar 4 and locking ring 5 by means of which it can be mounted in a wall 6 of a conduit or vessel 7 which contains a flowing corrosive medium 8. The element 2 is made of the material the effect on which of the corrosive medium 8 is to be monitored. For example it may be same as the material of the conduit or vessel if the intention is to monitor the state of the vessel or conduit 7, or it may be made of the same material as a corrodible component of a pump or other device (not shown) which is immersed in the corrosive medium 8. The base 3 of the probe 1 is hollow and contains within it a pair of leads 9 by means of which an electric current can be passed through the element 2, of the probe 1, a pair of leads 10 by means of which the voltage drop along a portion of the element 2 which includes the exposed portion can be determined and hence its resistance, and a lead 11 by means of which the resistance of a protected length 12 of the element 2 can be determined. Preferably the base 3 and, in particular the end 13 of the base 3 through which the element 2 passes, is made of an insulating material so as to minimise the risk of electrolytic corrosion of the element 2 occurring. A region 14 of the element 2 is rendered radioactive by bombarding it with a beam of protons prior to the insertion of the probe 1 into the wall 5 of the conduit or vessel 6. Such treatment produces a radioactive layer of material some tens of microns in depth. The activated region 14 of the element 1 can be chosen to be of any convenient size, for example as small as 3 mm$^2$ or as large as 500 mm$^2$. Also the element 2 can be in any convenient form such as a wire, a strip or a flattened tube.

The base 3 of the probe 1 is so shaped that the protected length 12 of the element 2 is within the vessel of conduit 6 containing the corrosive medium 8 so that it experiences the same conditions of temperature as does the exposed portion of the element 2. By measuring the ratio of the resistances of the two parts of the element 2, the effects of temperature changes which affect both parts of the element 2 are cancelled out, so that changes in the resistance of the exposed portion of the element 2 can be measured, and hence the amount of material removed from the exposed portion of the element 2 can be determined.

FIG. 2 shows how the probe 1 is used to detect and determine the presence of pitting corrosion of the element 2.

The probe 1 is installed in the wall 6 of the conduit or vessel 7 containing the corrosive medium 8, as has already been described. Down stream of the probe 1 there is positioned a radiation detector 21 which detects the growth of activity in the flowing corrosive medium.

The probe 1 produces an output signal which is related to changes in the resistance of the element 2. This signal is applied to a first electronic circuit 22 which produces a signal $s_1$ which is a measure of the rate of loss of material from the probe 1 as indicated by the change in its resistance. The radiation detector 21 produces an output signal which is a direct measure of the amount of material lost from the active region 12 of the element 2 of the probe 1. This signal is applied to a second electronic circuit 23 which produces a signal $s_2$ which is a measure of the rate of loss of material from the active region 12 of the element 2 of the probe 1. The signals $s_1$ and $s_2$ are compared in a comparator 24.

If the element 2 of the probe 1 corrodes uniformly, then the rate of loss of material as measured by the change in resistance of the element 2 of the probe will equal that measured by the loss of active material from the element 2 of the probe 1 because both methods measure absolutely the loss of material from the element 2 of the probe 1.

Should however, pitting corrosion of the element 2 of the probe 1 be taking place, then the two measured rates of removal of material from the element 2 of the probe 1 will differ, and this difference will be a measure of the amount of pitting corrosion taking place. The comparator 24 can be arranged to give a calibrated read-out, or a signal which can be recorded elsewhere or used to trigger an alarm.

We claim:

1. A method of detection and measurement of pitting corrosion in a corrosive environment, comprising the operations of exposing to the corrosive environment a corrodible element, a surface region of which has been rendered radioactive, measuring changes in a parameter of the element which is susceptible to the effects of corrosion of the element, simultaneously either measuring changes in the activity of the element or the growth of activity at a station downstream of the element, deriving from both sets of measurements indications of the rate of removal of corroded material from the element and comparing the indicated rates of removal of material from the element.

2. A method as claimed in claim 1, in which the surface region of the element has been rendered radioactive by bombardment with radiation having sufficient energy to cause nuclear reactions within the surface.

3. A method according to claim 2, wherein the radiation is a beam of protons.

4. A method as claimed in claim 1, in which the parameter of the element which is monitored is the electrical resistance of the element.

5. An apparatus for the detection and measurement of pitting corrosion in a corrosive environment, comprising means for supporting in a flowing corrosive environment a corrodible element, a surface region of which is arranged to be radioactive, means for measuring changes in a parameter of the element as a result of corrosion of the element and deriving therefrom a first signal representative of the rate of corrosion of the element, means for measuring either changes in the activity of the element or growth of activity at a station downstream of the element and deriving a second signal therefrom indicative of the rate of removal of active material from the element and means for comparing the first and second signals.

6. Apparatus according to claim 5, wherein the means for measuring changes in a parameter of the element comprises means for measuring changes in the electrical resistance of the element.

7. Apparatus according to claim 6, wherein there is included a second element identical to the corrodible element but positioned in a non-corrosive environment, means for maintaining the second element at the same temperature as the corrodible element, and means for comparing the electrical resistance of the two elements thereby to determine changes in the electrical resistance of the corrodible element arising from the corrosion of that element.

8. An apparatus according to claim 5, wherein the means for comparing the first and second signals is arranged to operate an alarm when the difference in the rates of corrosion indicated by the first and second signals exceeds a predetermined value.

* * * * *